United States Patent [19]
Braestrup et al.

[11] Patent Number: 4,751,222
[45] Date of Patent: Jun. 14, 1988

[54] 2,3,4,5-TETRAHYDRO-1H-3-BENZAZEPINES AND CNS AFFECTING USE THEREOF

[75] Inventors: Claus Braestrup, Roskilde; Peter H. Andersen, Vanløse; Poul Borrevang, Copenhagen; Frederik C. Grønvald, Vedbaek; Louis B. Hansen, Ballerup; Rolf Hohlweg, Kvistgård, all of Denmark

[73] Assignee: Novo Industri A/S, Bagsvaerd, Denmark

[21] Appl. No.: 853,891

[22] Filed: Apr. 21, 1986

[30] Foreign Application Priority Data

Apr. 22, 1985 [DK] Denmark ............................. 1804/85

[51] Int. Cl.⁴ .................... C07D 407/02; A61K 31/55
[52] U.S. Cl. .................................... 514/213; 540/594; 540/595
[58] Field of Search ........................ 540/594; 514/213

[56] References Cited

U.S. PATENT DOCUMENTS 3,393,192  7/1968  Walter et al. ................. 540/595
4,111,957  9/1978  Holden et al. ................ 540/594
4,284,555  8/1981  Gold et al. .................... 540/595

Primary Examiner—Glennon H. Hollrah
Assistant Examiner—D. B. Springer
Attorney, Agent, or Firm—Morris Fidelman; Franklin D. Wolffe

[57] ABSTRACT

Novel 2,3,4,5-tetrahydro-1H-3-benzazepines which in the 5-position have furyl, thienyl, pyridyl, or ring systems consisting of phenyl ortho condensed with a benzen, cyclohexan, cyclohexen, cyclopentan or cyclopenten ring wherein one of the carbon atoms may be exchanged with oxygen, sulphur or nitrogen, have interesting central nervous system and cardiovascular effects.

13 Claims, No Drawings

2,3,4,5-TETRAHYDRO-1H-3-BENZAZEPINES AND CNS AFFECTING USE THEREOF

BACKGROUND OF THE INVENTION

This invention relates to novel 2,3,4,5-tetrahydro-1H-3-benzazepines or salts thereof which are useful in the treatment of mental disorders.

In the last decade, intensive pharmacological research concerning benzazepines has taken place. The pharmacological properties of benzazepines depends to a large extend on the character of the substituents. For example, substituted benzazepines exhibiting neuroleptic, antiaggressive, antiparkinson and vascular effects, are known.

In U.S. Pat. No. 3,393,192 (Schering) derivatives of 1-phenyl-2,3,4,5-tetrahydro-1H-3-benzazepine having, inter alia, hydroxy, lower alkoxy or halogen in the 7- and/or 8-position are described. In European patent applications publication Nos. 5,298 and 5,299 corresponding 7-hydroxy derivatives are described. It is stated that these compounds have antipsychotic and antidepressive effects.

According to Life Sci. 31 (1982), 637 et seq., 2,3,4,5-tetrahydro-7,8-dihydroxy-1-phenyl-1H-3-benzazepine (designated SKF 38393) and 2,3,4,5-tetrahydro-9-chloro-7,8-dihydroxy-1-(4-hydroxyphenyl)-1H-3-benzazepine (designated SKF 82526) are selective but partial dopamine D1 agonists whereas 2,3,4,5-tetrahydro-7,8-dihydroxy-6-thiophenyl-1H-3-benzazepine (designated SKF 83742) is a selective D1 dopamine antagonist. Furthermore, it has been stated in Eur.J.Pharmacol. 91 (1983), 153 et seq., that R-8-chloro-7-hydroxy-2,3,4,5-tetrahydro-3-methyl-5-phenyl-1H-3-benzazepine (designated SCH 23390) is a selective D1 dopamine antagonist (see also European patent application No. 79200209.9).

In U.S. Pat. No. 4,187,314 (Smith Kline) 1-thienyl- or 1-furyl-2,3,4,5-tetrahydro-1H-3-benzazepines which, inter alia, contain hydroxy, lower alkoxy or lower alkanoyloxy in the 7- and 8-positions, are described. In the specific examples of such benzazepines given therein, the two substituents in the 7- and 8-position are identical. These benzazepines are stated to have peripheral and central dopaminergic activity.

SUMMARY OF THE INVENTION

It has now been found that novel 2,3,4,5-tetrahydro-1H-3-benzazepines of the general formula I

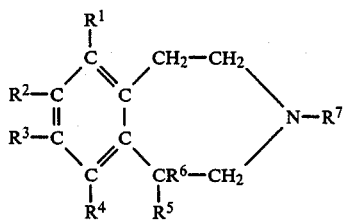

(I)

wherein $R^1$ represents hydrogen, halogen or alkyl with not more than 4 carbon atoms, $R^2$ represents halogen, trifluoromethyl, cyano, sulfo, sulfo(Cl-C2 alkyl) or carboxy, $R^3$ represents hydrogen, hydroxy, halogen, carboxy, mercapto, alkoxy with not more than 4 carbon atoms, (Cl-C2 alkyl)thio or hydroxy(Cl-C2 alkoxy), $R^4$ represents hydrogen or halogen, $R^5$ represents furyl, thienyl, pyridyl, or ring systems consisting of phenyl ortho condensed with a benzen, cyclohexan, cyclohexen, cyclopentan or cyclopenten ring in which rings one of the carbon atoms may be exchanged with oxygen, sulphur or nitrogen, and each of these ring systems may be substituted with one or more of the following groups: halogen, hydroxy or alkoxy with not more than 4 carbon atoms, $R^6$ represents hydrogen or methyl, and $R^7$ represents hydrogen or alkyl with not more than 4 carbon atoms, or salts thereof, exhibit useful pharmacological properties, especially effects on the central nervous system which, surprisingly, are superior to the effects of the known compounds. Benzazepines of formula I may be used as medicaments, for example, to treat schizophrenia and manic-depressive disorders.

Throughout this specification, the term "alkyl" with not more than 4 carbon atoms, when used alone or in a combination, i.e. alkoxy, designates a branched or straight alkyl group, for example methyl, ethyl, propyl, isopropyl and tert.butyl. By the term "alkoxy" is, preferably, intended methoxy and ethoxy. By the term "sulfo(Cl-C2 alkyl)" is intended sulfomethyl and 2-sulfoethyl. By the term "(Cl-C2 alkyl)thio" is intended methylthio and ethylthio. By the term "hydroxy(Cl-C2 alkoxy)" is intended hydroxymethoxy and 2-hydroxyethoxy. Halogen is chloro, bromo, fluoro and iodo, preferably chloro and fluoro.

According to the above definition, the substituent designated $R^5$ may, inter alia, be a ring system consisting of phenyl ortho condensed with another ring, namely with a benzen ring, with a cyclohexane ring, with a cyclohexene ring, with a cyclopentane ring or with a cyclopentene ring, and in each one of these rings one of the carbon atoms may be exchanged with a hetero atom, for example oxygen, sulphur or nitrogen and each one of these ring systems may be substituted with halogen, with hydroxy and/or with lower alkoxy. If the ring system is substituted, there is preferably only one substituent. Herein the term "ortho condensed" indicates that the phenyl ring in question has one of its sides in common with another of the specific rings mentioned above. Preferably, the substituent $R^5$ is phenyl which is ortho condensed with the aboves rings.

Specific examples of the substituent designated $R^5$ are furyl, thienyl, pyridyl, naphthyl, benzofuranyl, dihydrobenzofuranyl, benzothienyl, chromanyl, chromenyl, indolyl, indolinyl, indanyl, indenyl, 1,2,3,4-tetrahydronaphthyl, dihydronaphthyl, and quinolinyl, each of which may be substituted with halogen, hydroxy or lower alkoxy, for example chlorochromanyl, methoxychromanyl, hydroxychromanyl and hydroxybenzofuranyl.

The prior art does not disclose a particular biological advantage to the specific substitution pattern present in the structures of the benzazepines of this invention.

Compounds of formula I exhibit strong antidopaminergic effects. Thus, they inhibit potently stereotyped gnawing behaviour in mice induced by methylphenidate (for example using 60 mg/kg body weight, subcutaneously, one hour prior to observation, tested analogously as described in Acta Pharmacol.Toxicol. 31 (1972), 488). Further, the compounds of formula I inhibit conditioned avoidance response and amphetamine cue in rats.

Surprisingly, compounds of formula I act much more strongly at dopamine D1 receptors as labelled by $^3$H-SCH 23390 than at dopamine D2 receptors as labelled by $^3$H-spiperone.

Surprisingly, compounds of formula I are superior to previously described dopamine D1 antagonists, especially SCH 23390. Thus, compounds of formula I inhibit dopamine stimulated adenylate cyclase in homogenates from rat striatum with higher potencies than SCH 23390, see Example 7.

Further, SCH 23390 has been reported to exhibit a poor peroral adsorption and a short duration of action (vide Life Sci. 34 (1984), 1529). Compounds of formula I exhibit characteristics superior to those of SCH 23390.

Furthermore, compounds of formula I blocked dopaminergically-mediated behaviors (for example, stereotyped biting in rodents induced by dopamine-releasing agents).

The compounds of formula I may be present as enantiomer forms which may be resolved into R- or S-forms. This resolution may be conveniently accomplished by fractional crystallization, from appropriate solvents, of the salts of the compounds of formula I with optically active acids. When enantiomers are resolved, the desired pharmacological activity usually predominate in one of the enantiomers, most often in the R-form. Therefore, this invention includes all isomers, whether resolved or mixtures thereof.

Particularly valuable embodiments of this invention are non-toxic, pharmaceutically acceptable salts of benzazepines of formula I. Such salts include those derived from inorganic and organic acids such as hydrochloric, hydrobromic, sulfuric, phosphoric, methansulfonic, acetic, lactic, maleic, phthalic and tartaric acids. They may be prepared by standard procedures, such as mixing an acetone solution of the base with the stoichiometrical amount of the acid in a solvent, such as acetone, and evaporating the solvent to leave the desired salt as a residue.

In one group of preferred benzazepines of formula I, $R^1$ is hydrogen.

In a 2nd group of preferred benzazepines of formula I $R^2$ is halogen, preferably chloro or fluoro.

In a 3rd group of preferred benzazepines of formula I, $R^3$ is hydrogen, hydroxy, halogen or alkoxy.

In an 4th group of preferred benzazepines of formula I, $R^4$ is hydrogen.

In a 5th group of benzazepines of formula I, $R^5$ is phenyl ortho condensed with a benzen, cyclohexan, cyclohexen, cyclopentan or cyclopenten ring which may be substituted with halogen, hydroxy or methoxy.

In a 6th group of preferred benzazepines of formula I, $R^5$ is benzothienyl or 2,3-dihydrobenzothienyl.

In a 7th group of preferred benzazepines of formula I, $R^5$ is benzofuranyl or 2,3-dihydrobenzofuranyl.

In an 8th group of preferred benzazepines of formula I, $R^5$ is furyl, thienyl or pyridyl.

In a 9th group of preferred benzazepines of formula I, $R^5$ is chromanyl or chromenyl.

In a 10th group of preferred benzazepines of formula I, $R^5$ is indolyl or indolinyl.

In an 11th group of preferred benzazepines of formula I, $R^5$ is quinolinyl.

In a 12th group of preferred benzazepines of formula I, $R^6$ is hydrogen.

In a 13th group of preferred benzazepines of formula I, $R^7$ is hydrogen or methyl.

Examples of representative and preferred benzazepines of formula I are as follows:

(1) 8-chloro-7-hydroxy-3-methyl-5-(1-naphthyl)-2,3,4,5-tetrahydro-1H-3-benzazepine,
(2) 8-chloro-7-hydroxy-3-methyl-5-(2-naphthyl)-2,3,4,5-tetrahydro-1H-3-benzazepine,
(3) 8-chloro-7-hydroxy-3-methyl-5-(3-thienyl)-2,3,4,5-tetrahydro-1H-3-benzazepine,
(4) 8-chloro-7-hydroxy-3-methyl-5-(2,3-dihydrobenzofuran-4-yl)-2,3,4,5-tetrahydro-1H-3-benzazepine,
(5) 8-chloro-7-hydroxy-5-(3-thienyl)-2,3,4,5-tetrahydro-1H-3-benzazepine,
(6) 8-chloro-7-hydroxy-5-(1-naphthyl)-2,3,4,5-tetrahydro-1H-3-benzazepine,
(7) 8-chloro-7-methoxy-5-(2-naphthyl)-2,3,4,5-tetrahydro-1H-3-benzazepine,
(8) 8-chloro-7-hydroxy-3-methyl-5-(5-indanyl)-2,3,4,5-tetrahydro-1H-3-benzazepine,
(9) 8-chloro-7-methoxy-3-methyl-5-(5-indanyl)-2,3,4,5-tetrahydro-1H-3-benzazepine,
(10) 8-chloro-7-hydroxy-5-(4-benzofuranyl)-2,3,4,5-tetrahydro-1H-3-benzazepine,
(11) 8-chloro-7-hydroxy-3-methyl-5-(5-indenyl)-2,3,4,5-tetrahydro-1H-3-benzazepine,
(12) 8-chloro-7-hydroxy-3-methyl-5-(7-chromanyl)-2,3,4,5-tetrahydro-1H-3-benzazepine,
(13) 8-chloro-7-hydroxy-3-methyl-5-(3-pyridyl)-2,3,4,5-tetrahydro-1H-3-benzazepine,
(14) 8-chloro-7-hydroxy-5-(1,2,3,4-tetrahydronaphth-6-yl)2,3,4,5-tetrahydro-1H-3-benzazepine,
(15) 8-chloro-7-hydroxy-3-methyl-5-(2,3-dihydronaphth-4-yl)2,3,4,5-tetrahydro-1H-3-benzazepine,
(16) 8-chloro-7-hydroxy-3-methyl-5-(7-benzothienyl)-2,3,4,5-tetrahydro-1H-3-benzazepine.
(17) 8-chloro-7-hydroxy-3-methyl-5-(7-benzofuranyl)-2,3,4,5-tetrahydro-1H-3-benzazepine,
(18) 8-chloro-7-hydroxy-3-methyl-5-(2,3-dihydrobenzofuran-6-yl)-2,3,4,5-tetrahydro-1H-3-benzazepine,
(19) 8-chloro-7-hydroxy-3-methyl-5-(2,3-dihydrobenzofuran-7-yl)-2,3,4,5-tetrahydro-1H-3-benzazepine,
(20) 8-chloro-7-hydroxy-3-methyl-5-(2,3-dihydrobenzothien-7-yl)-2,3,4,5-tetrahydro-1H-3-benzazepine,
(21) 8-chloro-7-hydroxy-3-methyl-5-(5-chlorochroman-8-yl)2,3,4,5-tetrahydro-1H-3-benzazepine,
(22) 8-chloro-7-hydroxy-3-methyl-5-(8-chromanyl)-2,3,4,5-tetrahydro-1H-3-benzazepine,
(23) 8-chloro-7-hydroxyethoxy-3-methyl-5-(2,3-dihydrobenzo-furan-7-yl)-2,3,4,5-tetrahydro-1H-3-benzazepine,
(24) 8-chloro-7-hydroxy-3-methyl-5-(6-hydroxychroman-8-yl)2,3,4,5-tetrahydro-1H-3-benzazepine,
(25) 8-chloro-7-hydroxy-3-methyl-5-(5-hydroxybenzofuran-7-yl)2,3,4,5-tetrahydro-1H-3-benzazepine,
(26) 26) 8-chloro-7-hydroxy-3-methyl-5-(4-hydroxybenzofuran-6-yl)2,3,4,5-tetrahydro-1H-3-benzazepine,
(27) 8-chloro-7-hydroxy-3-methyl-5-(4-hydroxybenzothien-6-yl)2,3,4,5-tetrahydro-1H-3-benzazepine, and physiologically acceptable salts thereof.

In general, the 5-substituted-2,3,4,5-tetrahydro-1H-3-benzazepines of formula I may be prepared from 2-(phenethylamino)ethanols of the general formula IV

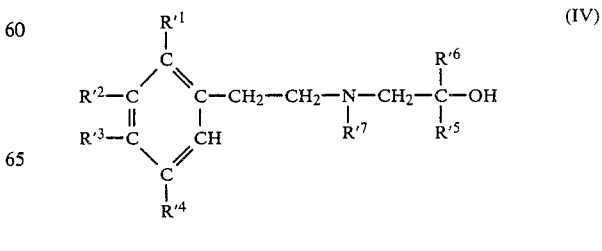

wherein R'¹, R'², R'³, R'⁴, R'⁵, R'⁶ and R'⁷ each are identical with R¹, R², R³, R⁴, R⁵, R⁶ and R⁷, respectively, or represent groups convertible thereto. These intermediary alcohols of formula IV may be prepared by heating equimolar quantities of an oxirane of the general formula III

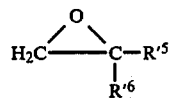   (III)

wherein R'⁵ and R'⁶ each are as defined above, with a β-phenethylamine of the general formula II

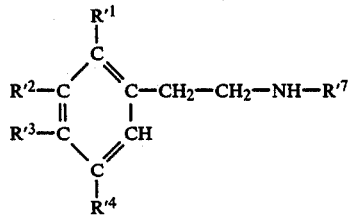   (II)

wherein R'¹, R'², R'³, R'⁴ and R'⁷ each are as defined above. Preferably, the condensation is performed at temperatures about 100° C. However, the reaction may take place within the interval between room temperature and about 105° C. The intermediary alcohols of formula IV may be isolated by usual operations such as crystallisation or distillation.

The 2-(phenethylamino)ethanols of formula IV are transformed into the desired benzazepines of formula I by means of an intramolecular cyclisation effected by reacting the 2-(phenethylamino)ethanol of formula IV with reagents such as polyphosphoric acid, sulfuric acid, trifluoroacetic acid or mixtures thereof or other similarly acting reagents. Preferably, the cyclisation is performed in sulfuric acid or in a mixture of sulfuric acid (1-20%) and trifluoroacetic acid at temperatures between about −10 and +20° C.

Benzazepines substituted in the 3-position are easily formed either by employing the corresponding, appropriate N-substituted phenethylamines or preferably alkylating the benzazepine of formula I in which R⁷ represents hydrogen.

The term "group convertible thereto" as used above designates, for example, the corresponding protected groups such as protected hydroxy, for example, protected with lower alkyl, for example methoxy or ethoxy, or benzyloxy. The protected groups can be deprotected in a manner known per se, for example, by hydrolysis or hydrogenation.

The starting materials for which the preparation is not described herein, are either known compounds or compounds which may be prepared in analogy with the preparation of known compounds or in analogy with known methods.

The benzazepines of formula I are useful because they possess pharmacological activity in animals, for example, in man. In particular, the compounds of formula I may be useful as antipsychotics. The benzazepines of formula I are administered to a host in need of treatment in an effective amount.

For the above use, the dosage will vary depending on the benzazepine of formula I employed, on the mode of administration and on the therapy desired. However, in general, satisfactory results may be obtained with a daily dosage of from 0.005 mg to about 2 mg per kg body weight, conveniently given in divided doses 2 to 5 times a day or in sustained release form. Usually, dosage forms suitable for oral administration comprise from about 0.5 mg to about 150 mg of the benzazepine of formula I admixed with a pharmaceutical carrier or diluent.

The benzazepines of formula I may be administered in pharmaceutically acceptable acid addition salt form. This invention also relates to pharmaceutical compositions comprising a benzazepine of formula I or a pharmaceutically acceptable salt thereof and, usually, such compositions also contain a pharmaceutical carrier or diluent. The compositions of this invention may be prepared by conventional techniques to be in conventional forms, for example, capsules or tablets.

The pharmaceutical carrier employed may be conventional solid or liquid carriers. Examples of solid carriers are lactose, terra alba, sucrose, talc, gelatin, agar, pectin, acacia, magnesium stearate and stearic acid. Examples of liquid carriers are syrup, peanut oil, olive oil and water. Similarly, the carrier or diluent may include any time delay material well known to the art, such as glyceryl monostearate or glyceryl distearate alone or with a wax.

If a solid carrier for oral administration is used, the preparation can be tableted, placed in a hard gelatin capsule in powder or pellet form or in the form of a troche or lozenge. The amount of solid carrier will vary widely but, usually, will be from about 25 mg to about 1 g. If a liquid carrier is used, the preparation may be in the form of a syrup, emulsion, soft gelatin capsule, sterile injectable liquid such as an ampul or an aqueous or non-aqueous liquid suspension.

The pharmaceutical compositions of this invention may be made following the conventional techniques of the pharmaceutical chemist involving mixing, granulating and compressing or variously mixing and dissolving the ingredients as appropriate to give the desired end product.

The route of administration may be any route which effectively transports the active compound to the appropriate or desired place, such as orally or parenterally, the oral route being preferred.

The nomenclature used herein complies with the IUPAC nomenclature with the proviso that, in an attempt to facilitate the reading of this specification, herein the position of the substituent designated R⁵ always has the number 5. According to the IUPAC nomenclature, this position is number 1 or 5 depending on how the benzazepine is substituted.

The features disclosed in the foregoing description and in the following examples and claims may, both separately and in any combination thereof, be material for realising the invention in diverse forms thereof.

The process of this invention is further illustrated by the following examples which, however, are not to be construed as limiting. Apart from Examples 1 and 2 illustrating processes for preparing starting material for preparing compounds of formula I, the examples illustrate some preferred embodiments.

EXAMPLE 1

(a) To a solution of 4.9 g of sodium hydride in 115 ml of dimethylsulfoxide was added 26.2 g of trimethylsulfoxoniumiodide over a period of about 30 minutes. 15.0 g of 5-indanylcarboxaldehyde was then added over a period of 5 minutes and the reaction mixture was stirred for 15 minutes at room temperature and then for 30 minutes at 50° C. The reaction mixture was poured into ice water and extracted twice with 200 ml of ether. The combined extracts were washed with water and dried over sodium sulfate (anhydrous).

Evaporation of the solvent left an oil which was fractionated under vacuum giving a colourless liquid, i.e., 5-indanyloxirane having the boiling point (hereinafter designated b.p.) 66° C. at 0.3 mm Hg.

In analogy with the above described method, the following compounds were prepared:

(b) (5-chlorochroman-8-yl)oxirane, b.p. 114° C. at 0.3 mm Hg.

(c) (3-thienyl)oxirane, b.p. 218° C., (d) (7-benzofuranyl)oxirane, b.p. 76°-78° C. at 0.1 mmHg, (e) (2,3-dihydrobenzofuran-7-yl)oxirane, b.p. 78° C. at 0.4 mm Hg, and (f) (1,2,3,4-tetrahydronaphth-6-yl)oxirane, b.p. 83° C. at 0.1 mm Hg.

EXAMPLE 2

(a) A mixture of 3.0 g of α-3-chlor-4-methoxy phenethylamine and 2.5 g of 5-indanyloxirane was stirred at 100° C. for 18 hours. 20 ml of acetonitrile was added to the still warm reaction mixture and crystallisation started immediately. The crystallisation was completed by chilling the mixture in ice water. The product was isolated by filtration, washed with cold acetonitrile and dried. Recrystallisation from acetonitrile gave N-(α-(3-chloro-4-methoxyphenethyl))-1-(5-indanyl)-2-aminoethanol with melting point (hereinafter designated m.p.) 138°-139° C.

In analogy with the above described method the following compounds were prepared:

(b) N-(α-(3-chloro-4-methoxyphenethyl))-1-(2-naphthyl)-2-aminoethanol, m.p. 150.5°-151° C., (c) N-(α-(3-chloro-4-methoxyphenethyl))-1-(1-naphthyl)-2-aminoethanol, m.p. 121.5°-124.5° C., (d) N-(α-(3-chloro-4-methoxyphenethyl))-1-(1,2,3,4-tetrahydronaphth-6-yl)-2-aminoethanol, m.p. 148°-150° C., and (e) N-(α-(3-chloro-4-methoxyphenethyl))-1-(3-thienyl)-2-aminoethanol, m.p. 68°-71° C.

In an analogous condensation of N-methyl-3-chloro-4methoxyphenethylamine and oxiranes, the following compounds were prepared:

(f) N-methyl-N-(α-(3-chloro-4-methoxyphenethyl))-1-(7-benzofuranyl)-2-aminoethanol, m.p. 89° C., (g) N-methyl-N-(α-(3-chloro-4-methoxyphenethyl))-1-(2,3-dihydrobenzofuran-7-yl)-2-aminoethanol, oil, purified by column chromatography on silicagel, (h) N-methyl-N-(α-(3-chloro-4-methoxyphenethyl))-1-(5-chlorochroman-8-yl)-2-aminoethanol, oil, purified by column chromatography on silicagel, (j) N-(α-(3-chloro-4-methoxyphenethyl))-1-(8-chromanyl)-2-aminoethanol, (k) N-(α-(3-chloro-4-methoxyphenethyl))-1-(6-methoxychroman-8-yl)-2-aminoethanol and (l) N-(α-(3-chloro-4-methoxyphenethyl))-1-(5-methoxybenzofuran-7-yl)-2-aminoethanol.

EXAMPLE 3

(a) 2.7 g of N-(α-(3-chloro-4-methoxyphenethyl))-1-(5-indanyl)-2-aminoethanol was dissolved in a mixture of 100 ml of trifluoroacetic acid and 2.5 ml of concentrated sulfuric acid. The reaction mixture was left for 1 hour at room temperature. Most of the trifluoroacetic acid was removed by evaporation in vacuum (about 10 mm Hg) and the residue was poured into an excess of a diluted sodium hydroxide solution (2 N). The alcaline suspension so obtained was extracted two times with 50 ml of dichloromethane. The organic extract was washed with saturated brine and dried over sodium sulfate (anhydrous). Evaporation of the dichloromethane left the desired product as an oil. This was dissolved in ether and precipitated as hydrochloride salt by addition of hydrochloric acid. After filtration and recrystallisation from methanol/water, 8-chloro-7-methoxy-5-(5-indanyl)-2,3,4,5-tetrahydro-1H-3-benzazepine hydrochloride, m.p. 140°-146° C., was obtained.

In analogy with the above described method, the following compounds were prepared:

(b) 8-chloro-7-methoxy-5-(2-naphthyl)-2,3,4,5-tetrahydro-1H-3-benzazepine hydrochloride, m.p. 245.5°-248.5° C., (c) 8-chloro-7-methoxy-5-(1-naphthyl)-2,3,4,5-tetrahydro-1H-3-benzazepine hydrochloride, m.p. 200° C., (d) 8-chloro-7-methoxy-5-(1,2,3,4-tetrahydronaphth-6-yl)2,3,4,5-tetrahydro-1H-3-benzazepine, m.p. 185°-195° C. (decomposition), (e) 8-chloro-7-methoxy-5-(3-thienyl)-2,3,4,5-tetrahydro-1H-3-benzazepine, oil, purified by column chromatography on silicagel, (f) 8-chloro-7-methoxy-5-(7-benzofuranyl)-3-methyl-2,3,4,5-tetrahydro-1H-3-benzazepine, m.p. 141°-142° C., (g) 8-chloro-7-methoxy-5-(2,3-dihydrobenzofuran-7-yl)-3-methyl-2,3,4,5-tetrahydro-1H-3-benzazepine, oil, purified by column chromatography on silicagel, (h) 8-chloro-7-methoxy-5-(5-chlorochroman-8-yl)-3-methyl-2,3,4,5-tetrahydro-1H-3-benzazepine hydrochloride, m.p. 181° C., (j) 8-chloro-7-methoxy-5-(3-thienyl)-3-methyl-2,3,4,5-tetrahydro-1H-3-benzazepine, oil, (k) 8-chloro-7-methoxy-3-methyl-5-(6-methoxychroman-8-yl)-2,3,4,5-tetrahydro-1H-3-benzazepine, (l) 8-chloro-7-methoxy-3-methyl-5-(8-chromanyl)-2,3,4,5-tetrahydro-1H-3-benzazepine, (m) 8-chloro-7-methoxy-3-methyl-5-(5-methoxybenzofuran-7-yl)2,3,4,5-tetrahydro-1H-3-benzazepine and (n) 8-chloro-7-methoxy-3-methyl-5-(3-pyridyl)-2,3,4,5-tetrahydro-1H-3-benzazepine.

EXAMPLE 4

(a) To a mixture of 40 ml of formic acid and 30 ml of 35% formaldehyde, 2.0 g of 8-chloro-7-methoxy-5-(5-indanyl)-2,3,4,5-tetrahydro-1H-3-benzazepine was added. The reaction mixture was refluxed for 4 hours and the solvent was evaporated. To the crude residue, a diluted sodium hydroxide solution (2 N) was added in excess and the mixture was extracted with ether. The organic phase was washed with water and brine and dried over sodium sulfate (anhydrous). The ether was evaporated in vacuo leaving the desired product as a sirup. The free base was dissolved in dry ether by adding a solution of hydrobromic acid in ether, the hydrobromide salt precipitated. This was recrystallised from trifluoroacetic acid/ether giving 8-chloro-7-methoxy-3-methyl-5-(5-indanyl)-2,3,4,5-tetrahydro-1H-3-benzazepine hydrobromide, m.p. 217°-222° C. (decomposition).

In analogy with the above described method, the following compounds were prepared:

(b) 8-chloro-7-methoxy-3-methyl-5-(2-naphthyl)-2,3,4,5-tetrahydro-1H-3-benzazepine hydrobromide, m.p. 251°-253° C., and (c) 8-chloro-7-methoxy-3-methyl-5-(1-naphthyl)-2,3,4,5-tetrahydro-1H-3-benzazepine hydrochloride, m.p. 200° C. (decomposition).

EXAMPLE 5

(a) 1.1 g of 8-chloro-7-methoxy-3-methyl-5-(5-indanyl)-2,3,4,5-tetrahydro-1H-3-benzazepine was dissolved in 10 ml of dichloromethane. The solution was cooled to −10° C. and 5 ml of boron tribromide was added. The reaction mixture was stirred while warming up to room temperature. After standing for 4 hours, the volatile components were removed by evaporation in vacuo and the residue was diluted with methanol at −10° C. Stripping with methanol gave 8-chloro-7-hydroxy-3-methyl-5-(5-indanyl)-2,3,4,5-tetrahydro-1H-3-benzazepine hydrobromide, m.p. 190°-200° C. (decomposition).

In analogy with the above described method, the following compounds were prepared:

(b) 8-chloro-7-hydroxy-3-methyl-5-(1-naphthyl)-2,3,4,5-tetrahydro-1H-3-benzazepine hydrobromide, m.p. 260° C. (decomposition), (c) 8-chloro-7-hydroxy-5-(2-naphthyl)-2,3,4,5-tetrahydro-1H-3-benzazepine hydrochloride, m.p. 180° C. (decomposition), (d) 8-chloro-7-hydroxy-3-methyl-5-(3-thienyl)-2,3,4,5-tetrahydro-1H-3-benzazepine, m.p. 200°-209° C., (e) 8-chloro-7-hydroxy-5-(3-thienyl)-2,3,3,5-tetrahydro-1H-3-benzazepine hydrobromide, m.p. 190° C. (decomposition), (f) 8-chloro-7-hydroxy-3-methyl-5-(5-chlorochroman-8-yl)-2,3,4,5-tetrahydro-1H-3-benzazepine, m.p. 230°-232° C., (g) 8-chloro-7-hydroxy-3-methyl-5-(2,3-dihydrobenzofuran-7-yl)-2,3,4,5-tetrahydro-1H-3-benzazepine, m.p. 225° C. (decomposition), (h) 8-chloro-7-hydroxy-3-methyl-5-(7-benzofuranyl)-2,3,4,5-tetrahydro-1H-3-benzazepine, m.p. 245° C., (j) 8-chloro-7-hydroxy-5-(1,2,3,4-tetrahydronaphth-6-yl)-3-methyl-2,3,4,5-tetrahydro-1H-3-benzazepine hydrochloride, m.p. 195°-200° C. (decomposition), (k) 8-chloro-7-hydroxy-3-methyl-5-(5-hydroxychroman-8-yl)-2,3,4,5-tetrahydro-1H-3-benzazepine hemimaleate, (l) 8-chloro-7-hydroxy-3-methyl-5-(5-hydroxybenzofuran-7-yl)-2,3,4,5-tetrahydro-1H-3-benzazepine hemimaleate, (m) 8-chloro-7-hydroxy-3-methyl-5-(8-chromanyl)-2,3,4,5-tetrahydro-1H-3-benzazepine hemimaleate and (n) 8-chloro-7-hydroxy-3-methyl-5-(3-pyridyl)-2,3,4,5-tetrahydro-1H-3-benzazepine.

EXAMPLE 6

(a) In 20 ml of 47% hydrobromic acid, 0.4 g of 8-chloro-7-methoxy-3-methyl-5-(2-naphthyl)-2,3,4,5-tetrahydro-1H-3-benzazepine was dissolved and the solution was refluxed for 1 hour. The reaction mixture was diluted with water and neutralized to a pH value of 8.5 by addition of sodium hydrogen carbonate. The obtained suspension was extracted with ethylacetate and dried with sodium sulfate (anhydrous). Evaporation of the solvent gave the product as an oil. This was dissolved in dry ether and after addition of hydrobromic acid (gaseous), 8-chloro-7-hydroxy-3-methyl-5-(2-naphthyl)-2,3,4,5-tetrahydro-1H-3-benzazepine hydrobromide, m.p. 260° C. (decomposition), was isolated.

In analogy with the above described method, the following compound was prepared:

(b) 8-chloro-7-hydroxy-5-(5-indanyl)-2,3,4,5-tetrahydro-1H-3-benzazepine hydrobromide.

EXAMPLE 7

Compounds of formula I as well as SCH 23390 were tested for their ability to inhibit dopamine stimulated adenylate cyclase in homogenates from rat striatum using the method described in Life Sci. 37 (1985), 1971 et seq., and the result appears from Table I where the compounds of formula I tested are racemic mixtures whereas SCH 23390 was tested as the pure R-(+)-isomer. $K_i$ is the affinity of the tested compound for the dopamine D1 receptor as estimated from Schild analysis.

TABLE I

| Test compound | $K_i$ (nM) dopamine stimulated adenylate cyclase |
|---|---|
| Example No. 5j | 21 |
| Example No. 5h | 6 |
| Example No. 5f | 10 |
| SCH 23390 | 40 |

EXMAPLE 8

8-chloro-7-hydroxy-3-methyl-5-(5-indanyl)-2,3,4,5-tetrahydro-1H-3-benzazepine and several other compounds of formula I were atoxic when given to rats and mice in a dosis of 100 mg/kg intraperitonealt.

It is expected that also the remaining compounds of formula I will have low acute toxicity.

EXAMPLE 9

| Preparation of Capsules. | |
|---|---|
| Ingredients | mg per capsule |
| 8-chloro-7-hydroxy-3-methyl-5-(5-indanyl)-2,3,4,5-tetrahydro-1H—3-benzazepine, HBr | 125 |
| Magnesium stearate | 2 |
| Lactose | 200 |

The above ingredients are thoroughly mixed and placed into hard gelatin capsules. Such capsules are administered orally to subjects in need of treatment from 1–5 times daily to induce dopaminergic activity.

EXAMPLE 10

| Preparation of Tablets. | |
|---|---|
| Ingredients | mg per tablet |
| 8-chloro-7-hydroxy-3-methyl-5-(5-indanyl)-2,3,4,5-tetrahydro-1H—3-benzazepine, HBr | 200 |
| Corn starch | 46 |
| Polyvinyl pyrrolidone | 12 |
| Magnesium stearate | 1 |

The benzazepin is thoroughly mixed with two thirds of the corn starch and granulated. The granules obtained are dried, mixed with the remaining ingredients and compressed into tablets.

The capsules or tablets thus prepared are administered orally. Similarly, other benzazepines of formula I can be used.

We claim:

1. 2,3,4,5-tetrahydro-1H-3-benzazepines of the general formula:

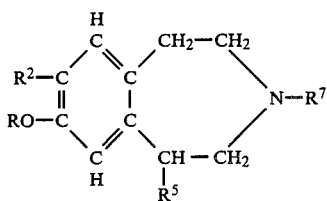

R is H, $R^2$ is halogen,
wherein $R^7$ is H or $C_{1-4}$ alkyl and
$R^5$ is a ring system consisting of phenyl ortho condensed with a benzene, cyclohexane, cyclohexene, cyclopentane, or with a cyclopentene ring, which may be substituted with halogen, hydroxy or methoxy, or furan, dihydrofuran, dihydropyran or halogenated dihydropyran ring.

2. Benzazepines according to claim 1 wherein $R^7$ is H or methyl.

3. A benzazepine according to claim 2 wherein $R^2$ is chloro, $R^5$ is 7-benzofuranyl and $R^7$ is methyl.

4. Benzazepines, according to claim 1, wherein $R^5$ is benzofuranyl or 2,3-dihydrobenzofuranyl.

5. Benzazepines, according to claim 1, wherein $R^5$ is chromanyl or chromenyl.

6. Benzazepines, according to claim 1, wherein $R^7$ is hydrogen or methyl.

7. The benzazepine according to claim 1, 8-chloro-7-hydroxy-3-methyl-5- (2,3 dihydrobenzofuran - 7-yl) - 2,3,4,5, - tetrahydro -1H-3 benzazepine.

8. 2,3,4,5-tetrahydro-1H-3-benzazepines of the general formula:

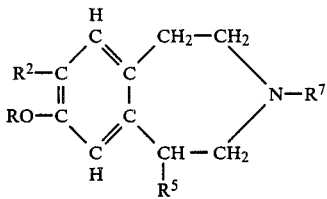

R is $CH_3$, $R^2$ is halogen, wherein $R^7$ is H or $C_{1-4}$ alkyl and
$R^5$ is a ring system consisting of phenyl ortho condensed with a benzene, cyclohexane, cyclohexene, cyclopentane, or cyclopentene ring, which may be substituted with halogen, hydroxy or methoxy or with a furan, dihydrofuran, dihydropyran or halogenated dihydropyran ring.

9. A benzazepine according to claim 8 wherein $R^2$ is chloro, $R^5$ is 7-benzofuranyl and $R^7$ is methyl.

10. A benzazepine according to claim 8 wherein $R^2$ is chloro, $R^5$ is 2, 3-dihydrobenzofuran - 7-yl.

11. A pharmaceutical composition containing a benzazepine of the below-given formula or a physiologically acceptable salt thereof:

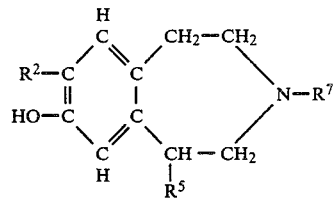

wherein
$R^2$ is halogen, $R^7$ is H or $C_{1-4}$ alkyl, and
$R^5$ is a ring system consisting of phenyl ortho condensed with a benzene, cyclohexane, cyclohexene, cyclopentane, or cyclopentene ring, which may be substituted with halogen, hydroxy, or methoxy, or with a furan, dihydrofuran, dihydropyran, or halogenated dihydropyran ring.

12. A pharamaceutical composition according to claim 11 containing between 0.07 mg and 70 mg of benzazepine per unit dosage.

13. A method for treating schizophrenia and manic-depressive disorders which comprises administering a pharmaceutically effective dosage of a benzazepine of the below-given formula or a physiologically acceptable salt thereof:

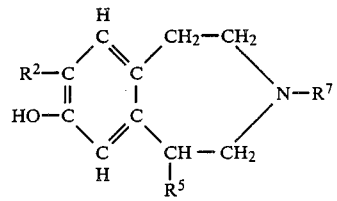

wherein
$R^2$ is halogen, $R^7$ is H or $C_{1-4}$ alkyl, and
$R^5$ is a ring system consisting of phenyl ortho condensed with a benzene, cyclohexane, cyclohexene, cyyclopentane, or cyclopentene ring, which may be substituted with halogen, hydroxy or methoxy, or with a furan, dihydrofuran, dihydropyran, or halogenated dihydropyran ring.

* * * * *